United States Patent
Altman

(10) Patent No.: US 11,285,334 B2
(45) Date of Patent: Mar. 29, 2022

(54) APPARATUS AND METHOD FOR TREATMENT OF DRY EYES

(71) Applicant: LUMENIS LTD., Yokneam (IL)

(72) Inventor: Hernan Altman, Kyriat Tivon (IL)

(73) Assignee: LUMENIS BE LTD., Yokneam (IL)

( * ) Notice: Subject to any disclaimer, the term of this patent is extended or adjusted under 35 U.S.C. 154(b) by 0 days.

(21) Appl. No.: 16/367,774

(22) Filed: Mar. 28, 2019

(65) Prior Publication Data

US 2019/0299016 A1 Oct. 3, 2019

Related U.S. Application Data

(60) Provisional application No. 62/666,162, filed on May 3, 2018, provisional application No. 62/718,134, filed on Aug. 13, 2018, provisional application No. 62/649,786, filed on Mar. 29, 2018.

(51) Int. Cl.
*A61N 1/40* (2006.01)
*A61N 5/06* (2006.01)

(52) U.S. Cl.
CPC .............. *A61N 1/40* (2013.01); *A61N 5/0613* (2013.01); *A61N 2005/0644* (2013.01); *A61N 2005/0651* (2013.01)

(58) Field of Classification Search
CPC .................... A61N 1/40; A61N 5/0613; A61N 2005/0651; A61N 2005/0644
See application file for complete search history.

(56) References Cited

U.S. PATENT DOCUMENTS

| | | | |
|---|---|---|---|
| 2008/0114424 A1* | 5/2008 | Grenon | A61F 9/00772 607/96 |
| 2013/0172959 A1 | 7/2013 | Azoulay | |
| 2015/0057701 A1* | 2/2015 | Kelleher | A61H 23/0236 606/204.15 |
| 2017/0172959 A1 | 6/2017 | Li et al. | |
| 2017/0299567 A1 | 10/2017 | Korb et al. | |

OTHER PUBLICATIONS

Search Report—Corresponding PCT Application No. PCT/IL2019/050370, dated Jul. 9, 2019, 7 pages.
Extended European Search Report—corresponding European Application No. 19774244.8, dated Dec. 8, 2021, 6 pages.

\* cited by examiner

*Primary Examiner* — Rex R Holmes
(74) *Attorney, Agent, or Firm* — ISUS Intellectual Property PLLC; Anthony Jason Mirabito

(57) ABSTRACT

A disposable/removable tip attachable on a distal end of a fiber bundle, allowing transmitting light energy from the fiber bundle to an eyelid and comprising a contact surface made of bio-compatible material, which allows to contact the eyelid and in addition an add-on device, comprising a fiber bundle, having a distal and proximal end, wherein a disposable/removable tip is attachable to the distal end, while the proximal end is connected to an optical coupler, designed for optical and/or energy coupling with a light-guide of a Meibomian gland expression (MGX) treatment device.

11 Claims, 3 Drawing Sheets

APPARATUS AND METHOD FOR TREATMENT OF DRY EYES

RELATED APPLICATIONS

This application is related to and claims priority to U.S. provisional application Ser. No. 62/649,786, filed Mar. 29, 2018, as well as U.S. provisional application Ser. No. 62/666,162, filed May 3, 2018, and 62/718,134, filed Aug. 13, 2018, the entire contents of all of which are herein incorporated by reference.

FIELD OF THE INVENTION

The present invention relates to an apparatus and method of treating dry eyes using a disposable/removable tip and an energy source that treats as well as heats a Meibomian Gland, the energy source being selected from among light sources, radio frequency (RF) sources and/or ultrasound (US) or other sources.

BACKGROUND OF THE PRESENT INVENTION

One main reason for dry eyes is blepharitis, a chronic inflammation of the eyelid margin. This is because if eyelid glands are chronically inflamed, they produce too little or even no secretions, which leads to an unstable tear film. The treatment of chronic blepharitis is not trivial, as it is often caused by pathogens such as bacteria and skin mites.

It has been shown that, for example, treatment with IPL (Intense Pulsed Light) light therapy or other has a long-lasting effect and bacteria and skin mites are successfully eliminated. IPL is a light pulse therapy that may be used to treat the inflammatory causes of dry eye, stimulate the eyelid glands and accelerate healing. Other light sources, such as LED or laser light, may be used. The use of a light source is for the purpose of generating heat, and causing photo-modulation, so as to heat up the area of a Meibomian Gland, so other sources of generating heat may be used.

U.S. Pat. Nos. 9,333,370 and 10,085,814, assigned to the assignee of the present invention, are directed to dry eye treatments and are herein incorporated by reference in their entireties.

In the course of treatment, several pulses of light may be delivered to a patient's eyelids. Care should be taken to avoid direct light entry into a cornea, as well as exposure of eyelashes to the energy (to avoid hair loss). In addition, direct heating of a cornea and other ocular surfaces should be avoided.

In the treatment of MGD (Meibomian Gland Dysfunction, or evaporative Dry Eye), Meibomian gland expression (MGX) is also a therapeutic approach, in which the glands are squeezed, generally after being heated through the use of IPL energy, LED energy or other energy, to force the meibum secretion out. Typically, this is achieved by pressing the eyelid from the outside with a finger, against a q-tip placed between the eyelid and the sclera. Sometimes, dedicated pincers or paddles are used for MGX.

SUMMARY OF THE PRESENT INVENTION

In an aspect, a method of treating ocular tissue by application of energy for treating dry eye includes: providing an energy generating device, the device further comprising a tip, and the tip has an extension that can be inserted posterior to an eyelid; the energy-generating device provides energy to the posterior of the eyelid; the method includes the steps of: inserting the tip posteriorly of the eyelid prior to applying energy to the posterior surface of the eyelid; and, applying energy from the energy device to the posterior surface of the eyelid.

In another aspect, a shielding extension is provided on the extension and includes a thermally insulative material such that energy not absorbed by a target tissue is prevented from reaching ocular tissue located posterior to the eyelid.

In a further aspect, the shielding extension is configured to be inserted posterior to an eyelid between the ocular conjunctiva and palpebral conjunctiva. The tip may be a removable tip. Further, the energy generating device is a light energy generating device. The light energy device may be one or more of: LED energy or IPL.

In yet a further aspect, the energy device may be one or more of: RF energy or ultrasonic energy.

In an aspect, a method of treating ocular tissue during application of energy for treating dry eye may include: providing an energy generating device, the device further comprising a tip which may be generally U-shaped and configured to be inserted both anterior and posterior to an eyelid; the energy-generating device provides energy to one or both of the anterior and the posterior of the eyelid; the method comprising the steps of: inserting the tip anteriorly and posteriorly of the eyelid prior to applying energy to one or more of the anterior and posterior surfaces of the eyelid; and, applying energy from the energy device to one or more of the anterior and posterior surfaces of the eyelid.

In another aspect, a shielding extension is provided on the posterior portion of the tip and is comprised of a thermally insulative material such that energy not absorbed by a target tissue is prevented from reaching ocular tissue located posterior to the eyelid.

In a further aspect, the energy generating device further comprises a shaft having a distal end portion; the shaft may be movable toward and away from the anterior of the eyelid; and, the energy generating device may be mounted on the distal end portion of the shaft; the method includes the steps of: moving the shaft distally to contact the anterior of the eyelid; activating the energy-generating device to provide energy to the posterior of the eyelid; and, moving the shaft further distally to apply pressure to the eyelid positioned between the distal portion of the shaft and the tip extension posterior of the eyelid.

An objective of embodiments herein is to eliminate or at least alleviate the problems discussed above.

An embodiment relates to a disposable/removable tip (DT) attachable on the (distal) end of a fiber bundle, allowing transmitting light energy from the fiber bundle to an eyelid and comprising a contact surface made of bio-compatible material, which allows to contact the eyelid. Preferably the disposable/removable tip allows transmitting light energy from the fiber bundle to the posterior surface of the eyelid.

For this purpose, the DT preferably comprises a bent or inflected structure of a transparent or translucent material. Preferably the DT has a spatula distal tip bent down with respect to the optical fiber bundle.

Even more preferably the DT comprises means (e.g. opaque or reflecting portions of the DT) for protecting the eyelashes, hair follicle or an eye against damage caused by light or high temperature.

According to another preferred embodiment of the invention, the DT comprises a distal tip and a proximal tip which form a clamp preferably bent downwards with respect to the fiber bundle and adapted to encompass or grasp an eyelid therebetween.

A disposable/removable tip has a lot of advantages compared to a tip fixed to a medical device or light guide. But however it should be clear that the treatment can also be administered with a fixed tip having the same features as described above.

Another embodiment relates to an add-on device, comprising a fiber bundle, having a distal end and a proximal end, wherein a disposable/removable tip is attachable to the distal end, while the proximal end is connected to an optical coupler, designed for optical and/or energy coupling with light source, like a Lumenis M22 handpiece or other IPL devices.

Another embodiment relates to a system of the disposable/removable tip and the add-on device.

Another aspect of the invention is a method for treating blepharitis or Meibomian gland dysfunction comprising the steps of treating a patient's eyelids with IPL/Light using a disposable tip as described above and preferably also executing Meibomian gland expression (MGX).

Yet another aspect of the invention is the use of a protective contact lens that is inserted prior to treatment that protects a cornea and other ocular surfaces from the light and/or heat sources used in the course of treatment for dry eyes by providing thermal isolation through use of the protective contact lens as described herein.

Yet another aspect of the invention is to connect the tip to a vacuum source causing the tip to "stick" to the eyelid. For this purpose the tips described above and below in the drawings may comprise (a) through hole(s) in the soft material of the tips that is/are connected to a vacuum source on a proximal end having (a) distal suction ending(s) in the vicinity of a patient's posterior or anterior eyelid. The vacuum source can be included in the add-on device or the IPL/light source.

BRIEF DESCRIPTION OF THE DRAWINGS

Some embodiments of apparatuses and/or methods will be described in the following by way of example only, and with reference to the accompanying figures, in which.

DETAILED DESCRIPTION OF THE PRESENT INVENTION

Various exemplary embodiments will now be described more fully with reference to the accompanying drawings in which some example embodiments are illustrated.

Anatomical terms of location, like distal and proximal refer to the devices described not to a patient (except where mentioned otherwise). In consequence, a distal end of a device may be closer to a patient, than a proximal end of the device.

Figure 1:
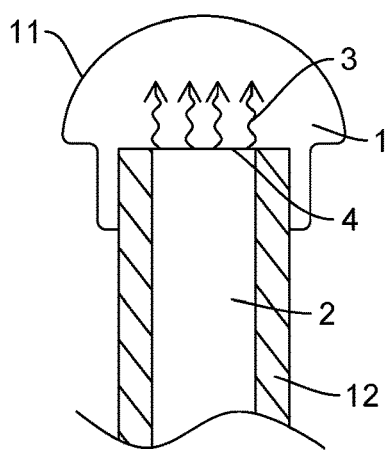
FIG. 1 shows a disposable tip with a round, soft shape.

In general, referring now to FIG. 1, a disposable or removable tip (DT) 1 may be constructed of a transparent or translucent material, such as silicone, which allows delivery of light energy (preferably IPL or laser) to an eyelid 5.

The DT 1 may be provided in clean/sterile state i.e. packaging, for example one for each eye, to allow hygienic treatment for every patient.

During the procedure, the DT packaging is opened and the DT 1 is mounted over the distal end 4 of the fiber bundle 2. Mounting may be accomplished by adhesive, force-fitted (friction between sides of the fiber bundle 2 and an annular part of the DT surrounding the fiber bundle 2) or form-fitted (e.g. by a thread).

The fiber bundle 2, in particular an optical fiber cable, also known as a fiber optic cable, is an assembly similar to an electrical cable, but containing one or more optical fibers that are used to carry light, which light source may be Intense Pulse Light (IPL) or another light source, such as LEDs. The fiber bundle 2 may be surrounded by a protective tube 12, which may have a reflective inner surface.

In several of the following embodiments, a semi-transparent material can be used to manufacture the DT 1, for example, by doping or tinting the material. One such material is silicone. By using such a technique, a part of the light energy will be absorbed by the DT 1, thus heating it and resulting in delivery of this heat to a surrounding patient's tissue, for example an eyelid. For some applications, heat has been shown to be a useful treatment modality for MGD, alleviating some Dry Eye symptoms. According to another aspect of the invention the DT (not shown), the DT may include a temperature sensor for sensing the temperature of the tip itself and/or a patient's eyelid while in use.

If heating is not desired or is achieved by other means, a transparent material may be used to forward as much of the light energy as possible.

The treatment process might comprise a first step, wherein an eyelid 5 is heated up with a heating element or a light source as described above. In a second step—after the eyelid has been heated a predetermined time or the temperature of the eyelid has exceeded a predetermined threshold—the outside of the eyelid is touched and pressure is put on the eyelid 5, which is now clamped between the tip and a piece or stop, like a Q-Tip, that is positioned in back of the eyelid 5. According to one alternative, the heating can be maintained during the second step. According to further alternatives, the steps of heating and exerting pressure on an eyelid can be conducted simultaneously or intermittently.

The materials used may be bio-compatible, for example silicone, to allow light forwarding from the fiber bundle 2 and delivery to a patient's skin/tissue, for example, safe contact with an eyelid 5 or even an eye. This applies at least for light transmitting parts of the DT 1 or parts coming into contact with a patient, like the surface of a contact zone facing the patient. Other parts of the DT1 might comprise different types of materials.

FIG. 1 depicts a design which provides a more comfortable treatment experience for a patient. The light beam 3 may be transmitted via the fiber bundle 2 and to the distal end 4 of the fiber bundle 2 and then into the disposable tip (DT) 1. This DT 1 transmits heat from the light beam 3 via a contact surface to the patient's eyelid. A round, soft tip 11 allows a comfortable interface for the physical contact between the tip 11 and the eyelid 5. The soft tip 11 may also be hemispherically shaped (shown in FIG. 2a, 3a) so that, when contacting the eyelid, the softness of the material distributes the force and in consequence the pressure on the eyelid 5.

Figure 2A:
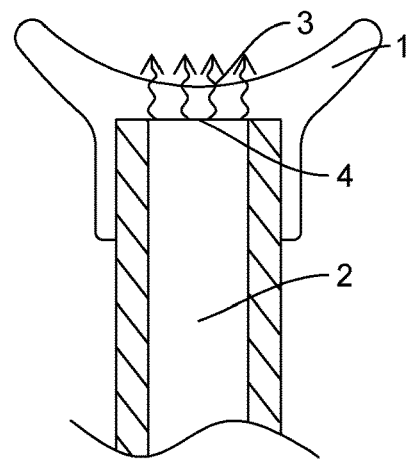
FIG. 2a shows a disposable tip with a concave shape.

FIG. 2a depicts a concave-shaped DT 1 which enables better conformation to the natural curvature of the eyelid 5, as a mere surface contact would do. This allows stable delivery of light and heat from a light source, as well as the capability to generate a vacuum between the DT 1 and the eyelid 5, effectively attaching the DT 1 to the eyelid 5 (similar to the principle of a vacuum cup).

Figure 2B:
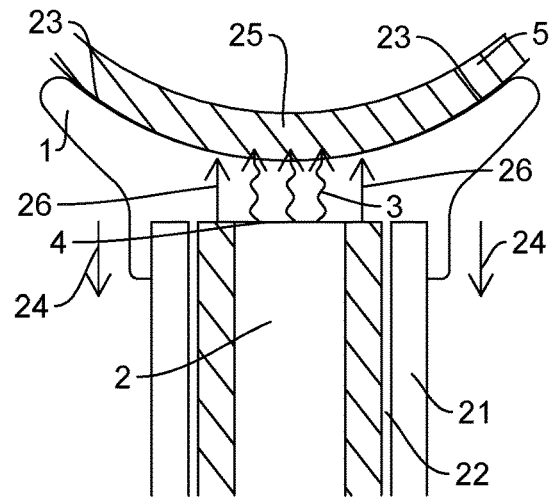
FIG. 2b shows an alternative disposable tip with a concave shape.

FIG. 2b depicts an enhanced version of the DT 1 of FIG. 2a to allow usage of the DT 1 for MGX. The fiber bundle 2 is positioned within a lumen 22 of a tube 21 or shaft. The tube 21 surrounds the fiber bundle 2. The tube has one end aligned with the distal end 4 of the fiber bundle 2 while the other end of the tube 21 has an open end with the fiber bundle 2 proceeding further proximal. A handle (not depicted) for manually moving the tube 21 axially/translational may be attached proximal to the distal tip.

The DT 1 is attached to the external tube 21, thus covering also the centered fiber bundle 2. Therefore, the DT 1 may overlap the tube 21 in a proximal direction, like a cap. The attachment (e.g. force-fitted) between the DT 1 and tube 21 is of such a strength, which allows movement within the DT 1, in particular shearing forces, induced by moving the fiber bundle 2 inside the lumen 22 in a distal direction relatively to the tube 21.

To treat MGX, the tube 21 or DT 1 is gently pulled away from the eyelid 5 or/and at the same time pushing the fiber bundle 2 towards the eyelid 5. This causes a change of the radius of the concave shaped contact surface, as the fiber bundle 2 presses towards the center of the concave contact surface, while the outer part of the concave contact surface is pulled away by the tube 21, which is connected at the outer part of the DT 1.

This causes pulling the eyelid's 5 external surface (where the outer region 23 of the DT 1 is located), by an outward force 24, due to the vacuum between the DT 1 and eyelid 5, while pushing a center region 25 of the eyelids, aligned with the fiber bundle 2, by an inward force 26.

The effect is that a first region (center region 25) of the eyelid 5 is moved in one direction while a second region (outer region 23), which is very close to the first region, is moved to the opposite direction. This causes a shearing force on the eyelid 5 which leads to a squeezing effect, effectuating MGX.

Advantageously, a DT 1 is provided which is easy to assemble and in addition to IPL treatment allows MGX treatment.

Figure 3A:
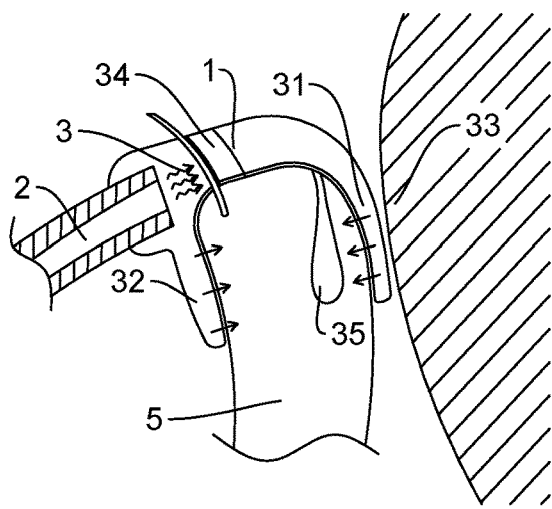
FIG. 3a shows a disposable tip with an eyelid clamp.

FIG. 3a depicts another embodiment of a DT 1 in a cross section of the eyelid 5 with the DT 1 shown placed on both sides of the eyelid 5. In this embodiment, the DT 1 includes both an inner (proximal) 32 and an outer (distal) tip 31 of a clamp. A gap 34 separates tips 31 and 32 and may have a variable distance so that the distance between the tips may be changed. For treatment, the outer tip 31 (distal) of the DT 1 is located between the eyelid 5 and the sclera 33. The eyelid 5 is placed between both tips 31, 32 and the distance between the tips 31, 32 is reduced to create a squeezing force suitable for effecting MGX. The reduction in distance between the tips may be accomplished with a sliding or other mechanism (to be discussed below in connection with FIGS. 3C and 3D). The sliding or other action that varies the distance between tips 31 and 32 may be manual or may be automated using a motor or other mechanism under manual control or under control of a suitable controller. A pressure-sensing device may be incorporated so that the degree of force exerted on the eyelid clamped between tips 31 and 32 is controllable.

Advantageously, this embodiment allows a more typical delivery method of MGX, in particular, using a squeezing force (two opposite forces aligned) instead of a shearing force (two opposite forces parallel misaligned). Both embodiments allow, in addition, light/heat treatment. The combination of providing MGX and light/heat therapy has proven to be very efficient.

Figure 3B:
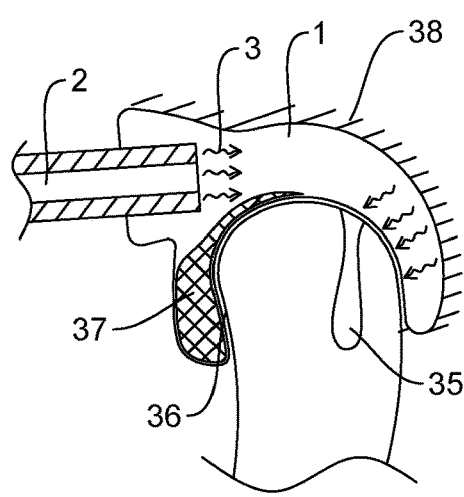
FIG. 3b shows a disposable tip with light guidance.

FIG. 3b depicts a similar embodiment or even an enhancement of the previous embodiment of FIG. 3a with the goal of a more efficient energy delivery to the target organs (the Meibomian glands 35) as well as to protect eyelashes 36. In the DT 1 with the distal tip 31 and the proximal tip 32 forming a clamp as described before, the proximal tip 32 may be opaque or comprise an opaque plastic 37 preferably at least covering part of the surface which—in the case of use—touches the eyelid in the region of the eyelashes. This prevents the eyelashes from being damaged.

The outer surface (not facing the patient's eyelid) of the DT 1 and especially of the distal end of the DT 1 may be coated with a highly reflective layer 38. The reflective layer 38 prevents light from traveling beyond the distal end of the tip, by reflecting the light/heat back into the tip which may amplify the amount of light/heat reaching the posterior surface of the eyelid.

Advantageously, the light/heat energy can be delivered to the posterior surface of the eyelid 5 in the vicinity of the Meibomian glands 35. An additional advantage of this design, due to the reflective layer 38 is the avoidance of light flashes to the patient's eye, thus increasing patient's comfort and safety. A further device for the protection of the patient's eye, such as the cornea, will be described below in connection with FIG. 5.

The treatment process might comprise a previous/first step, where the eyelid 5 is heated up with a heating element (not displayed) or by the light device itself, as explained previously. The heated portion is, according to the construction of this embodiment, at the proximal part of the distal tip 31, which faces the Meibomian gland 35. Heating exactly this spot is a result of the reflection of energy by the reflective layer 38. By clamping the eyelid in the embodiments shown in FIGS. 3a and 3bt, no additional tool, like a q-tip, is necessary.

The typical human eyelid thickness is 3-4 mm, with the eyelashes 36 located on the outside (related to the human head) and the Meibomian glands 35 located on the inside, occupying 400-600 μm of the eyelid 5 sagittal cross-section. According to this, the distance between the two tips 31, 32 has to be adapted.

Figure 3C:
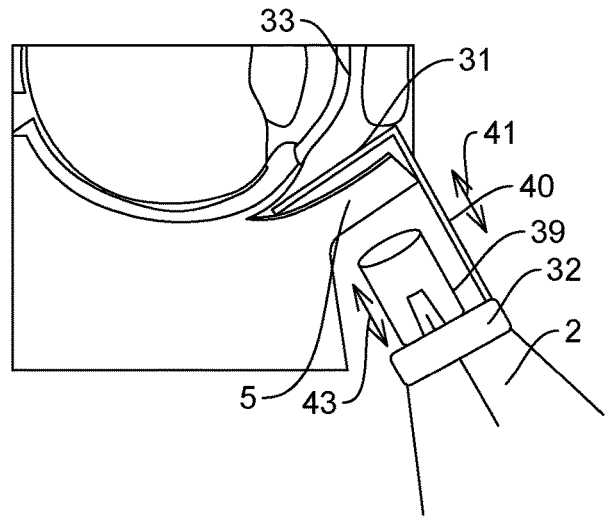
FIG. 3c shows a disposable tip with an eyelid clamp moved with a telescope.

FIG. 3c depicts another enhancement of the previous embodiments, more clearly displaying the movement possibilities to perform MGX. A telescoping element 40 connects the distal tip 31 and the proximal tip 32 of the DT 1, which can telescope in directions 41 so that the proximal tip 32 is movable towards or away from the eye. A cylindrical tube 39 is mounted on the distal side of the proximal tip 32 or fiber bundle 2. During treatment, the cylindrical tube 39 is brought into contact with the eyelid 5 either by sliding the telescoping element 40 in a direction to decrease the distance between the two tips 31, 32 and, thus, clamping the eyelid 5 and performing MGX. Alternatively, the telescoping element 40 may be fixed and the cylindrical tube 39 moved in directions 43 as shown in FIG. 3c to move the tube 39 into contact with the eyelid 5, such that the eyelid is clamped between the distal tip 31 and the tube 39.

Figure 3D:
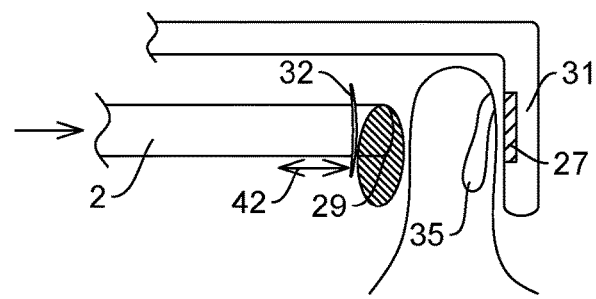
FIG. 3d shows a disposable tip with an eyelid clamp moved with a sledge.

FIG. 3d depicts a similar arrangement, wherein, instead of a telescoping element 40, a proximal tip 32 mounted on the distal end of a fiber bundle 2 may be moved in directions 42 towards and away from the eyelid 5. This can be accomplished by a sliding element or elements as described in connection with FIG. 3c, wherein a part connected with the distal tip 31 slides onto a part connected with the proximal tip 32 in a direction towards or away from the eyelid 5. An end element 29, which may be similar to tip 1 of FIGS. 1, 2a and 2b, may be mounted on the distal end of the proximal tip 32. It is to be understood that, while in FIG. 3d a fiber bundle 2 is shown, that the source of light/heat may be mounted on the proximal end 32 itself so that no fiber bundle may be required.

Additionally, FIG. 3d shows a heating/light element 27 which may be mounted on or within distal tip 31. The heating/light element 27 may be used to heat the eyelid 5 and the contained Meibomian gland 35 either in conjunction with the heat/light from the source of light/heat from the fiber 2 or otherwise so that the gland is heated from both sides of the eyelid 5.

The arrangement of capturing the eyelid between the tips 31 and 32 may lead to less force being put by the distal tip 31 on a patient's eye as in the embodiment, for example, of FIG. 1, and this in turn may lead to less discomfort to the patient.

Figure 4:
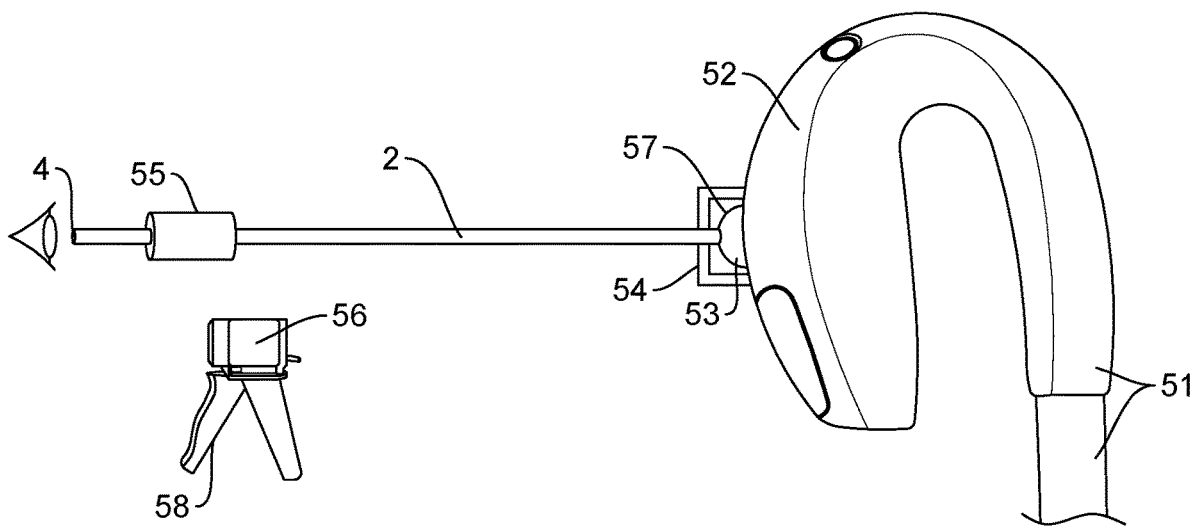
FIG. 4 shows a system for forwarding light energy.

FIG. 4 depicts a system in which the treatment end of an available MGD treatment device 51, like the Lumenis M22 IPL, may be more easily handled and manipulated close to the treatment area. This embodiment comprises an add-on device that is attachable to the handpiece 52 via optical lightguide or lightguide interface 53. It allows light energy delivery through the fiber and out from the distal end 4 of the fiber 2 around an eye's orbit (upper and lower eyelids 5).

The proximal end of the fiber bundle 2 is attached to an optical coupler or interface 54, which allows each individual fiber to spread out, for better coverage of the lightguide 53 surface area, to allow better optical and energy coupling. This part may be multi-use due to the need for accuracy and the high quality/expensive materials required.

The distal end 4 of the fiber bundle 2 may include an interface (such as handle adapter 55), for example made of plastic. An ergonomic handle 56 may be attached thereto, allowing comfortable positioning of the distal end 4 of the fiber bundle 2 to small areas around the eyes, without the burden of having to manually hold and manipulate the handpiece 52 of the MGD treatment device 51.

Otherwise, without the handle 56, the operator may hold the distal end 4 of the bundle 2 like a pen while treating the patient. In order that the distal end 4 maintains its shape, a stiffening element, which may be a harness or a relatively stiff tube, in which the distal end 4 is threaded, may be used so that the distal end 4 can be directly applied over an eyelid 5 to be treated, without fear of the distal end 4 bending and emitting light energy to undesired areas around an eye.

The fiber bundle 2 employed may also incorporate a filter to allow for wavelength selection as well as act as an energy damper to reduce the original fluence emitted by the MDG treatment device 51 to acceptable levels for eyelid 5 treatment. The add-on device allows an adjustability or variability in fluences different to the one(s) provided by the MDG treatment device 51, thus providing the possibility for more effective treatments.

Depending on the use case, the add-on device or fiber bundle 2 may be disposable or reusable. The fiber bundle 2 may be distributed in a sterile package.

Parts of the add-on device like the bundle interfaces 54, 55 or the DT switch may degrade after sterilization or cleaning so that this add-on device would become unusable. This feature would prevent accidental double use of this single use item.

The fiber bundle 2 may contain 20-50 fibers with a plastic casing, to achieve a treatment area (bundle end 4) of ~5 mm diameter.

The distal end 4 of the fiber bundle 2 itself may optionally be covered by a DT 1, e.g. by a soft, biocompatible material, like silicon, as described in various previous embodiments. By covering the relatively hard distal end 4 with the DT 1 (soft cap), the DT 1 may even contact a patient's eyelid 5, without causing discomfort to the patient or harm the tissue.

The handle 56 may include an operating button 58 to trigger an IPL pulse and or a switch for controlling the clamp mechanism. In such a case, the handle needs to include an interface, e.g. an electrical connection to the MDG treatment device. Alternatively, the IPL pulse generation may be controlled from the handpiece 52 or from a footswitch operatively connected to the add-on device.

In addition, as may be seen on 3a-d, an L-shaped distal tip 31, as previously described, may be removable mounted on the distal end 4 of the fiber bundle 2 or on the distal end of the ergonomic handle 56. The distal tip 31 may function as a shield that is inserted behind the eyelids to protect the eye while the upper and/or lower eyelids 5 are treated.

The proposed invention/embodiments would allow for:

1. Better access to structures around the eye, including the upper or lower eyelid 5, while avoiding unintended exposure of the eyelashes 36 or the cornea, which may result from use of a large lightguide 53 such as the current M22 IPL handpiece 52.

2. Ease of use, through the dedicated, lightweight ergonomic handle 56. This is enabled by the fact that the current IPL handpiece 52 fulfills the energy and cooling functions, while the proposed handle's 56 sole function would be to hold the fibers' distal end 4 and bring it into direct contact above or below the eyelids 5 (i.e. it only fulfills the ergonomic/usability functions).

3. A sterile, disposable design.

4. A modular solution, which allows for the use of the current handpiece 52 for treatment of Rosacea and supports the current MGD protocol delivered from tragus to tragus. Most MGD patients also suffer from Rosacea, making it necessary to treat them for this indication to alleviate the MGD symptoms.

5. Fluence reduction for improved safety around the eyelid 5 area through the design of the fiber bundle 2 as an energy damper (current M22 IPL has a lower limit on delivered fluence, which may be considered by some as too high for MGD in certain cases).

6. More specific selection of light spectrum, for improved treatment efficacy, by the use of a doped fiber as a low-pass filter, in addition to the built-in high-pass filter in the IPL's handpiece 52.

Figure 5:
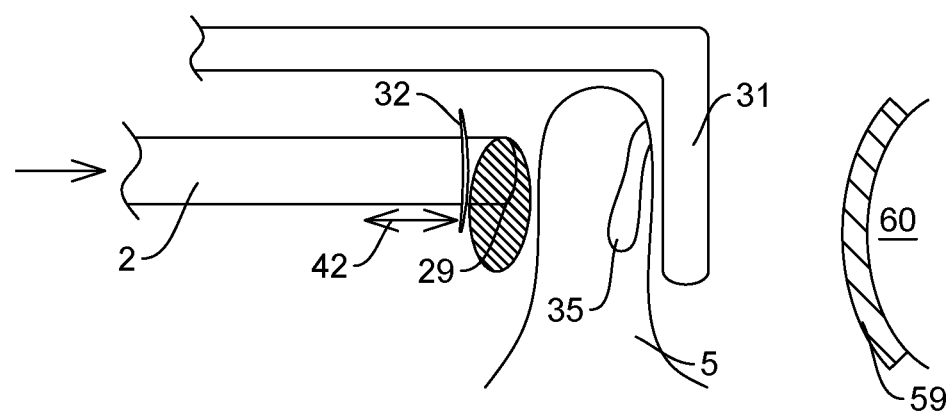
FIG. 5 shows an insert for the protection of the patient's eye.

Turning now to FIG. 5, that figure shows an additional element 59 that may be interposed between the tip 31 and the eye 60. The purpose of the element 59 is to protect the eye against any stray light/heat from causing damage to the eye 60, either due to excess light or the heat generated by the light (or other) source. The element or shield 59 may be in the form of a contact lens, such as a soft-type contact lens, with no optical changing capabilities, that the doctor may place on the eye to be treated for dry eye. The shield 59 may be a tinted with a biocompatible dye or ink and may be chosen to be completely opaque to the wavelengths of light generated by a light source selected to heat the eyelid. The lenses may vary in size and on extent of coverage of the eye, and thus may be corneal, semi-scleral or scleral, depending on the treatment to be provided. The element may even be completely opaque and maybe made of a material that reflects light and/or provides heat insulating properties so that the eye is not subjected to excess heating which might cause damage to the eye being treated. The shield may also be a disposable that maybe discards after each treatment or of a design that can be sterilized and reused.

REFERENCE NUMBERS 1 disposable/removable tip (DT)
2 fiber bundle
3 IPL (Intense Pulse Light)/light beam
4 distal end of fiber bundle
5 eyelid
11 round/soft tip
12 protective tube
21 tube
22 lumen
23 outer region
24 outward force
25 center region
26 inward force
27 heating element
29 end element
31 outer (distal) tip
32 inner (proximal) tip
33 sclera
34 intersecting gap
35 Meibomian glands
36 eyelashes
37 opaque plastic
38 reflective layer
39 cylindrical tube
40 telescope
41 expanding/shortening direction
42 moving direction
43 moving direction
51 MGD treatment device
52 handpiece
53 lightguide
54 optic coupler
55 handle adapter
56 handle
57 proximal end
58 operating button
59 shield
60 eye

I claim:

1. A method of treating ocular tissue by application of energy for treating dry eye, the method comprising:
   providing an energy generating device, the device comprising:
   (i) a tip, the tip being generally U-shaped and having two portions, one portion being configured to be inserted anterior to an eyelid, the other portion being configured to be inserted posterior to an eyelid,
   (ii) an energy element configured to provide energy to the anterior portion and to the anterior of the eyelid, and
   (iii) a highly reflective layer within the posterior portion of the tip and configured to reflect energy back to the posterior surface of the eyelid;
   inserting the U-shaped tip anteriorly and posteriorly of the eyelid prior to applying energy to the anterior portion of the eyelid; and,
   applying energy from the energy element directly to the anterior portion of the eyelid and by reflection to the posterior surface of the eyelid.

2. The method of claim 1, wherein a shielding extension is provided on on the posterior portion of the tip comprised of a thermally insulative material such that energy not absorbed by a target tissue is prevented from reaching ocular tissue located posterior to the eyelid.

3. The method of claim 1, wherein the U-shaped tip extension is configured to be inserted posterior to an eyelid between the ocular conjunctiva and palpebral conjunctiva.

4. The method of claim 1, wherein the tip is a removable tip.

5. The method of claim 1, wherein the energy generating device is a light energy generating device.

6. The method of claim 5, wherein the light energy device is one or more of: LED energy or IPL.

7. The method of claim 1, wherein the energy device is one or more of: RF energy or ultrasonic energy.

8. A method of treating ocular tissue during application of energy for treating dry eye, the method comprising:
   providing an energy generating device, the device further comprising:
   (i) a tip, the tip being generally U-shaped, and being configured to be inserted both anterior and posterior to an eyelid,
   (ii) an energy elements on the tip and being configured to provide energy directly to both the anterior and to the posterior of the eyelid, and
   inserting the tip anteriorly and posteriorly of the eyelid prior to applying energy to one or more of the anterior and posterior surfaces of the eyelid; and,
   applying energy from the energy device directly to the anterior and to the posterior surfaces of the eyelid.

9. The method of claim 8, wherein a shielding extension is provided on the posterior portion of the tip and is comprised of a thermally insulative material such that energy not absorbed by a target tissue is prevented from reaching ocular tissue located posterior to the eyelid.

10. The method of claim 1, wherein the energy generating device further comprises a shaft having a distal end portion;
    the shaft being movable being movable toward and away from the anterior of the eyelid;
    the energy generating device being mounted on the distal end portion of the shaft;
    the method comprising the steps of:
    moving the shaft distally to contact the anterior of the eyelid;
    activating the energy-generating device to provide energy to the anterior of the eyelid; and,
    moving the shaft further distally to apply pressure to the eyelid positioned between the distal portion of the shaft and the tip portion posterior of the eyelid.

11. The method of claim 8, wherein the energy generating device further comprises a shaft having a distal end portion;
    the shaft being movable being movable toward and away from the anterior of the eyelid;
    the energy generating device being mounted on the distal end portion of the shaft;
    the method comprising the steps of:
    moving the shaft distally to contact the anterior of the eyelid;
    activating the energy-generating device to provide energy to the anterior and to the posterior of the eyelid; and, moving the shaft further distally to apply pressure to the eyelid positioned between the distal portion of the shaft and the tip portion posterior of the eyelid.

* * * * *